United States Patent [19]

Hölscher

[11] Patent Number: 4,657,022
[45] Date of Patent: Apr. 14, 1987

[54] ELECTRODE ARRANGEMENT FOR TRANSDUCERS

[75] Inventor: Uvo Hölscher, Stockelsdorf, Fed. Rep. of Germany

[73] Assignee: Drägerwerk AG, Fed. Rep. of Germany

[21] Appl. No.: 794,625

[22] Filed: Nov. 4, 1985

[30] Foreign Application Priority Data

Nov. 6, 1984 [DE] Fed. Rep. of Germany ....... 3440401

[51] Int. Cl.⁴ ............................ A61B 5/00; A61B 5/04
[52] U.S. Cl. ..................................... 128/635; 128/640
[58] Field of Search .................. 128/635, 639–642; 204/403

[56] References Cited
U.S. PATENT DOCUMENTS

| 4,281,659 | 8/1981 | Farrar et al. | 128/635 |
| 4,538,617 | 9/1985 | Jensen | 128/635 |

FOREIGN PATENT DOCUMENTS 0077054 10/1982 European Pat. Off. .
2930663 2/1981 Fed. Rep. of Germany ...... 128/635

Primary Examiner—Lee S. Cohen
Attorney, Agent, or Firm—McGlew and Tuttle

[57] ABSTRACT

An electrode arrangement in transducers for the combined measurement of various physiological quantities includes adhesion areas for connecting the arrangement to the skin. To increase adhesion strength and to provide a better electric insulation between measuring electrodes in the transducer, a ring body which carries the electrodes is provided with an adhesive area which includes an electrolytically or electrically conductive doping zone that extends up to an outer edge piece of the ring body. The edge piece is made of electrically insulating material, one of the measuring electrodes is put into electric contact with the skin through the doping zone.

5 Claims, 1 Drawing Figure

U.S. Patent
Apr. 14, 1987
4,657,022
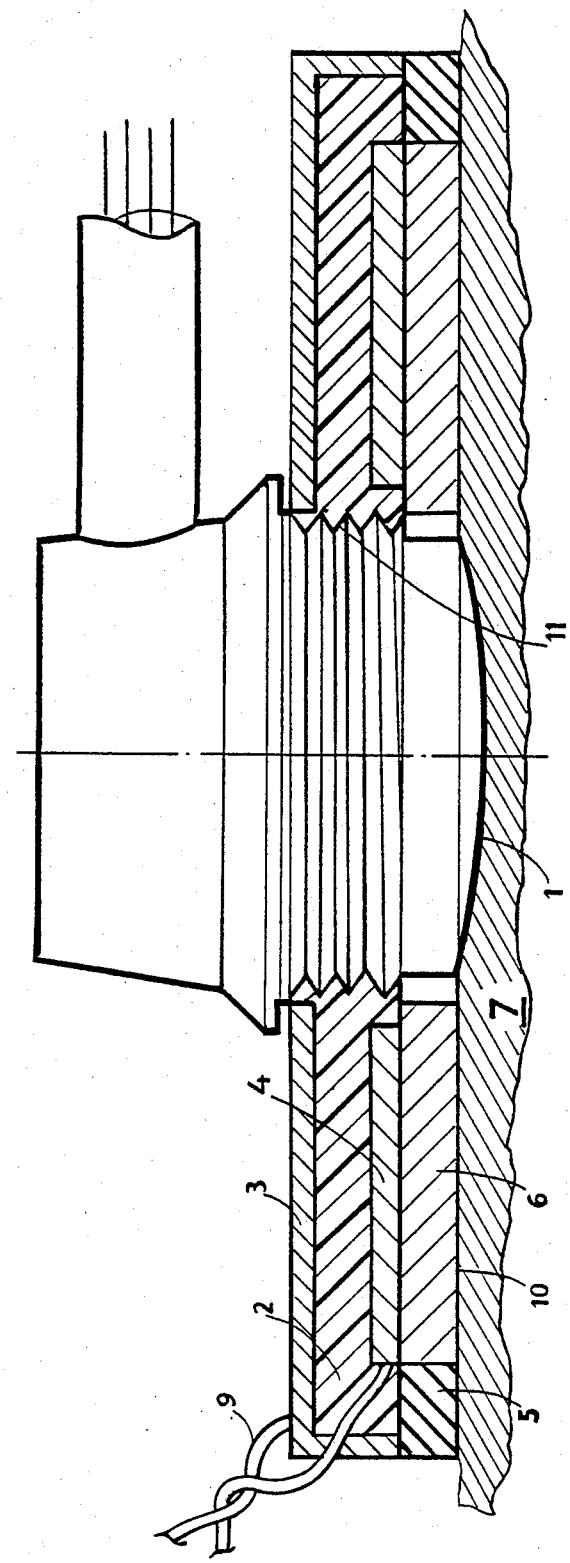

ELECTRODE ARRANGEMENT FOR TRANSDUCERS

FIELD AND BACKGROUND OF THE INVENTION

The invention relates in general to electrode arrangements for transducers and in particular to a new and useful transducer for the combined measurement of various physiological quantities or parameters, which has a measuring head for recording a first physiological quantity and means for measuring a second physiological quantity. These means comprises a first measuring electrode located on one side of a ring body adjacent the measuring head, and a second counter-electrode on another side of the ring body spaced away from the measuring head.

Such an electrode arrangement for a transducer is known from European Patent application No. 0077054. In this transducer, besides the electrode arrangement for recording a first physiological quantity, which is provided in a measuring head body, an additional electrode arrangement is provided which comprises a first electrode on one side of the measuring head body facing toward a contact area, and a second electrode on the back or opposite side of the measuring body. With such a transducer, the transcutaneous oxygen partial pressure is measured, for example, via the first electrode arrangement and the additional electrode arrangement measures a second physiological quantity such as the cardiac action potential (EKG). The first electrode on the side of the measuring head body toward the contact area serves as the measuring electrode, and the second electrode on the back of the measuring head body as counter-electrode.

In the known electrode arrangement, an adhesive is applied on the bearing surface of the measuring head body provided for that purpose, the measuring electrode being surrounded by this adhesive. Such gluing is to establish an electrical insulation of the measuring electrode from the counter-electrode. However, only a small outer region of the total bearing surface is available for this bonding, so that its durability is limited. Durability is diminished further by the fact that body fluids can penetrate into the adhesive layer, thus reducing the adhesion force of the adhesive layer.

In order to utilize adhesive areas next to the electrode surfaces which are to be connected to the skin, two apparently contradictory requirements must be fulfilled. For one thing, the surfaces of the electrodes should be as large as possible so as to present as low an impedance as possible toward the skin, and hence not to be susceptible to trouble or interference. In addition the adhesive areas of the transducers should be as large as possible, so that in practical use they cannot move away from the contact area even under relatively great tensile and shearing stress. On the other hand, the total area of the adhesive area plus the electrode surface should be as small as possible, so that the transducer can be applied to body parts having small surfaces such as the part of the exposed head of an unborn child (so called fetal monitor). Generally, electrodes for recording physiological quantities are provided with an ion conducting gel for contacting with the skin. The adhesion force of such gels, however, are not sufficient for relatively great loads. When used with comparatively bulky and heavy transducers for transcutaneous oxygen measurement, such gels do not ensure reliable adhesion conditions on the contact area under the complicated conditions occurring in practice.

In a transducer which is suitable for measuring physiological quantities, the adhesive strength is further reduced because a recess is needed for the electrode arrangements in the adhesive area.

SUMMARY OF THE INVENTION

The object of the present invention is to provide a design for the contact adhesion area on a transducer for the combined measurement of plural physiological quantities, and to provide an appropriate attachment on the skin in such a way that the electrode for recording a second physiological quantity and the adhesion area for the attachment of the transducer do not hinder one another and have a total size which is tolerable in practice.

According to the invention, a ring body which carries the measuring head has a side which is connectable to the skin by a glue-on or adhesion area which comprises an electrolytically or electrically conducting adhesive layer or doping zone that extends up to an outer edge piece on the ring body consisting of electrically insulating material. The measuring electrode of the ring body is in electrical contact with the skin through the adhesive layer.

With the construction of the adhesive layer according to the invention, it is ensured that the electrode for measuring a bioelectrical quantity, as for example for taking an electrocardiogram, is separated from its counter-electrode by an insulating region. In this way neither body fluids, which might occur in the form of amniotic fluid at birth when the transducer is used on a fetus, nor other liquids approaching from the outside can cause a shortcircuit between the measuring electrode and the counter-electrode or a reduction of the potential difference between the two electrodes. The large area adhesion of the transducer provides for safe retention even under increased tensile stresses and transverse forces along the adhesion. The region of the adhesion area of the electrically insulating material increases, in an advantageous manner, the electric insulation of the conductive doping zone of the adhesive layer from its surrounding.

The electrode arrangement according to the invention may appropriately be designed so that the ring body has a central threaded recess which serves for the attachment of known transducers tor transcutaneous oxygen measurement.

According to other features of the invention the counter-electrode is provided on the back of the ring body. This makes it possible to employ the ring body with its measuring electrode and counter-electrode, if needed, for measuring one physiological quantity only, such as the cardiac action potential. For this purpose, the measuring head for the transcutaneous measurement is replaced by a blind plug fitted into the central recess.

Accordingly another object of the invention is to provide an electrode arrangement for transducers which comprises a measuring head having a measuring surface for sensing a first physiological parameter, a ring body connected to said measuring head and having a first surface facing in the same direction as said measuring surface as well as a second surface facing in an opposite direction, an edge member connected to said first surface of said ring body around an edge of said ring body, a first electrode connected to said first surface of said ring body, a second electrode connected on said second surface of said ring body and spaced away from said first electrode, an adhesive layer made of electrolytically or electrically conductive material disposed over said first electrode and on said first surface up to said edge member, said layer having an outer adhesion area for adhesion to skin and for establishing an electrical connection between the skin and said first electrode.

Another object of the invention is to provide an electrode arrangement for a transducer that can be used to measure more than one physiological quantity or parameter, which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the acompanying drawings and descriptive matter in which a preferred embodiment of ths invention is illustrated.

BRIEF DESCRIPTION OF THE DRAWING

The only FIGURE in the drawing is a sectional view partly in side elevation of a transducer utilizing the electrode arrangement of the present invention.

DESCRIPTION OF THE PREFERRED EMBODIMENT

The transducer shown in the drawing has a measuring head 1 for measuring a first physiological quantity, for example the transcutaneous oxygen partial pressure. Surrounding it is a ring body 2, which receives the measuring head 1 by a threaded part 11 in a central recess of body 2. An electrode arrangement for measuring a second physiological quantity, as for example the cardiac action potential is provided on the ring body 2. The further electrode arrangement contains a measuring electrode 4, which is set in an annular cutout or recess in the ring body 2. On a side of the ring body 2 away from the measuring electrode 4, a counter-electrode 3 is provided. Both electrodes 3 and 4 are connected via connecting lines 9 to an evaluating unit (not shown). The ring body 2 with the measuring head 1 contained therein, is attached, via a glue-on or adhesive area 10, on the skin 7 for recording of data. The glue-on area 10 is bounded by an adhesive, electrically insulating edge member 5. A doping zone 6 is disposed between edge member 5 and measuring head 1, which contains a known electrolytically or electrically conducting pressure-sensitive adhesive. This adhesive establishes an electrical connection betweek skin 7 and measuring electrode 4.

The edge member 5 can be made for example, of non-conductive adhesive or other insulating material and may be elastic or rigid. Known materials which are either electrolytically or electrically conductive can be used as adhesive layer 6. Ring body 2 is also made of electrically insulating material such as plastic or other suitable material to electrically separate and insulate electrodes 3 and 4 from each other. The measuring head 1 has a measuring surface which is meant to be in contact with skin 7 for taking a measurement therefrom. The head itself is of known design and includes leads which are connected to known equipment for measuring the physiological quantity or parameter, such as oxygen partial pressure noted above.

While a specific embodiment of the invention has been shown and described in detail to illustrate the application of the principles of the invention, it will be understood that the invention may be embodied otherwise without departing from such principles.

What is claimed is:

1. An electrode arrangement for a transducer comprising, a measuring head having a measuring surface for measuring a first physiological quantity, a ring body connected to and surrounding said measuring head, said ring body having a first surface facing in the same direction as said measuring surface and a second surface spaced away from said first surface, an edge member made of insulating material connected to said first surface and adjacent an outer edge of said ring body, said edge member extending outwardly of said first surface, a first electrode connected to said first surface of said ring body, a second electrode connected to said second surface of said ring body and spaced away from said first electrode, said first electrode forming a measuring electrode and said second electrode forming a counter-electrode, and an adhesive layer of material which is electrically conductive disposed on said first electrode over said first surface of said ring body and extending to said edge member, said adhesive layer having an adhesion area facing the same direction as said measuring surface of said measuring head whereby said adhesion area and said measuring surface may contact skin from which physiological parameters are to be measured, said adhesion layer establishing electrical connection between the skin and said first electrode.

2. An electrode arrangement according to claim 1, wherein said ring body includes a central threaded recess therein, said measuring head being threaded into said recess.

3. An electrode arrangement according to claim 1, wherein said second surface of said ring body is on a back of said ring body opposite from said first surface.

4. An electrode arrangement according to claim 3, wherein said ring body includes a threaded recess, said measuring head being threaded in said threaded recess.

5. An electrode arrangement according to claim 4, wherein said edge member has substantially the same thickness as said adhesive layer in a direction extending normally to said first surface.

* * * * *